(12) United States Patent
Patrickus

(10) Patent No.: US 7,300,401 B2
(45) Date of Patent: Nov. 27, 2007

(54) COMBINED MOUTH EXPANDING AND SALIVA EJECTING DENTAL APPARATUS

(76) Inventor: John E. Patrickus, 3131 Nicolet Dr., Green Bay, WI (US) 53411

( * ) Notice: Subject to any disclaimer, the term of this patent is extended or adjusted under 35 U.S.C. 154(b) by 0 days.

(21) Appl. No.: 11/091,026

(22) Filed: Mar. 28, 2005

(65) Prior Publication Data

US 2005/0227199 A1    Oct. 13, 2005

Related U.S. Application Data

(60) Provisional application No. 60/560,503, filed on Apr. 8, 2004.

(51) Int. Cl.
*A61B 1/32* (2006.01)
*A61C 17/06* (2006.01)

(52) U.S. Cl. .......................... 600/238; 600/242; 433/93

(58) Field of Classification Search ................. 433/93, 433/94, 140; 600/238, 239, 242
See application file for complete search history.

(56) References Cited

U.S. PATENT DOCUMENTS

| | | | |
|---|---|---|---|
| 342,042 A | | 5/1886 | Rowney |
| 730,128 A | | 6/1903 | Jordan |
| 951,130 A | | 3/1910 | Jordan |
| 1,868,653 A | * | 7/1932 | Abraham ..................... 433/29 |
| 3,049,806 A | * | 8/1962 | Cofresi ......................... 433/93 |
| 3,735,491 A | * | 5/1973 | Pabalan, Jr. ................. 433/93 |
| 3,916,880 A | * | 11/1975 | Schroer ....................... 600/205 |
| 4,019,255 A | | 4/1977 | Cohen et al. |
| 4,053,984 A | * | 10/1977 | Moss ........................... 433/93 |
| 4,167,814 A | | 9/1979 | Schubert |
| 4,259,067 A | | 3/1981 | Nelson |
| 4,695,253 A | | 9/1987 | Tysse |
| 5,037,298 A | | 8/1991 | Hickham |
| 5,460,524 A | * | 10/1995 | Anderson ..................... 433/93 |
| 5,513,986 A | | 5/1996 | Feltham et al. |
| 5,516,286 A | | 5/1996 | Kushner |
| 5,873,718 A | | 2/1999 | Sullivan |
| 6,022,214 A | * | 2/2000 | Hirsch et al. ................. 433/29 |
| 6,267,591 B1 | | 7/2001 | Barstow |
| 6,575,746 B2 | | 6/2003 | Hirsch et al. |
| D496,995 S | | 10/2004 | Dorfman |

* cited by examiner

*Primary Examiner*—Cary E. O'Connor
(74) *Attorney, Agent, or Firm*—Joseph S. Heino; Patrick M. Bergin

(57) ABSTRACT

A combined mouth retracting and saliva ejecting device has a forward suction portion, a right cheek retractor portion, a left cheek retractor portion, and a rearward suction portion, the device being configured to be placed within the mouth of a dental patient. The device is constructed of a single piece of rigid, but resilient, tubular material, the material having an elastomeric memory. The device is tubular and has a cylindrical or other shape cross section and can be constructed of material so as to be either disposable or nondisposable, the nondisposable version being capable of heat or chemical sterilization. The device can be made in almost any size to accommodate the wide variety of patients that it may be used with, including children. The device may also incorporate fiber optic technology whereby light transmissive fibers are imbedded into the device to allow for selective illumination within the patient's mouth as either a light source for light curable dental compounds or for enhanced visualization.

8 Claims, 2 Drawing Sheets

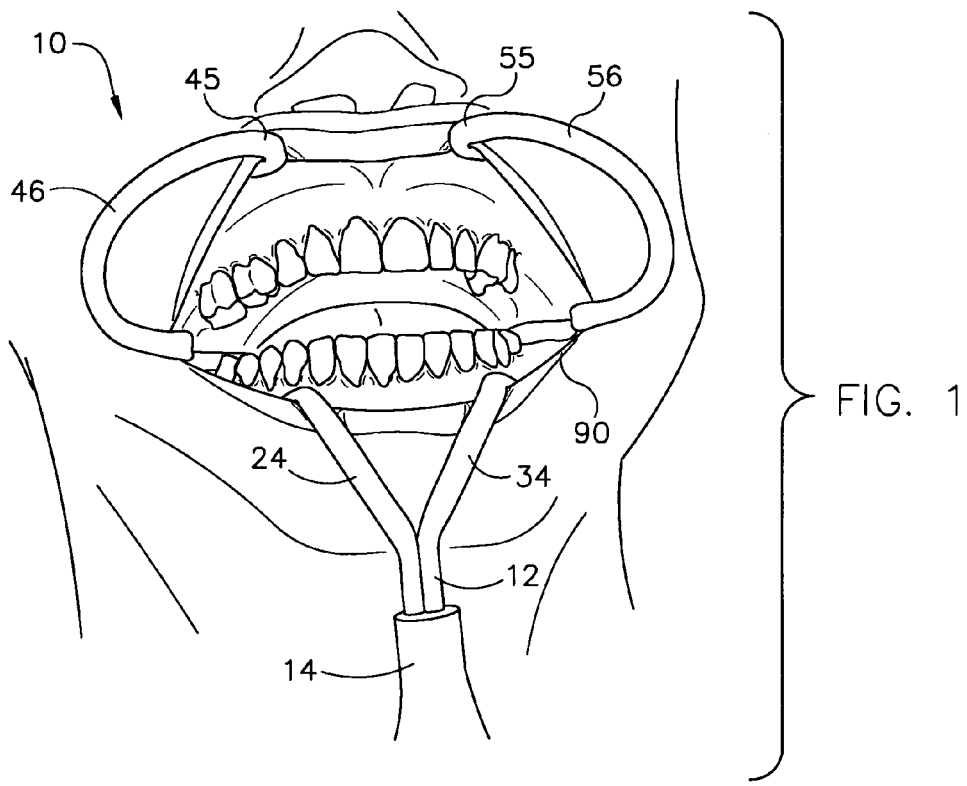
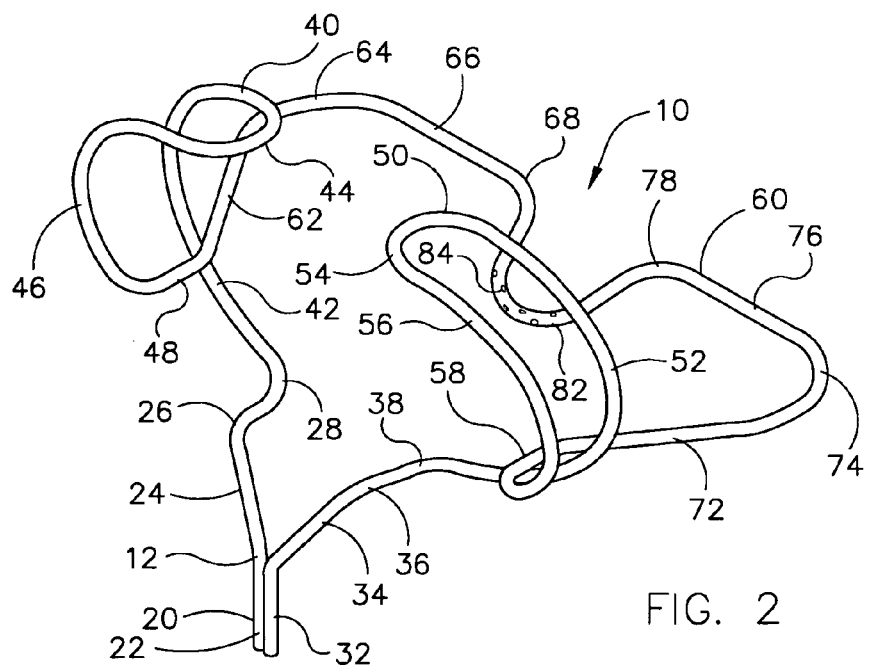

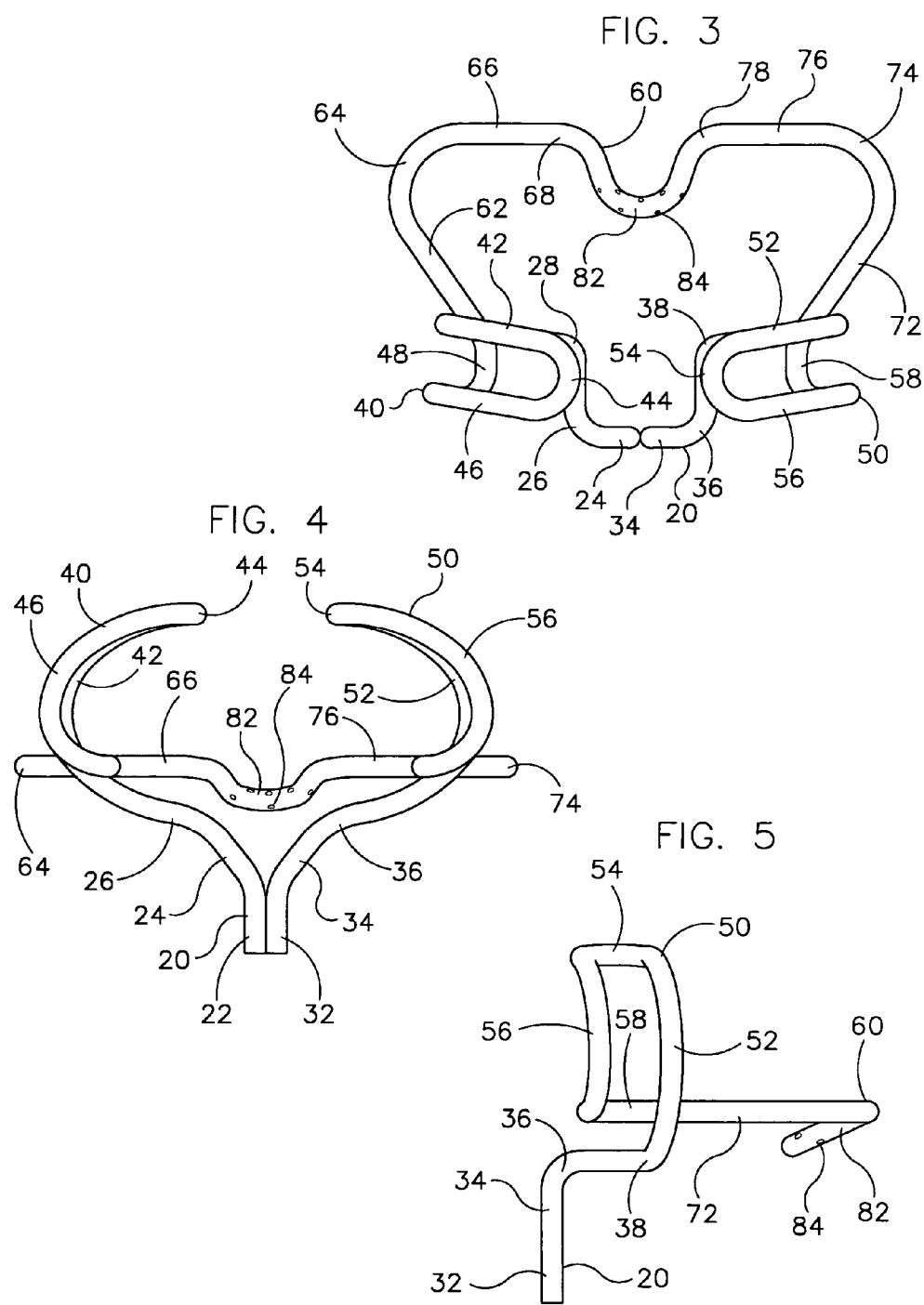

COMBINED MOUTH EXPANDING AND SALIVA EJECTING DENTAL APPARATUS

This application claims the benefit of U.S. Provisional Patent Application Ser. No. 60/560,503, filed Apr. 8, 2004.

FIELD OF THE INVENTION

This invention relates generally to dental procedures and to instruments and devices used by professionals during the performance of dental procedures. More particularly, it relates to a combined mouth expanding and saliva ejecting device to provide access to the dentist's working field and to help keep that working field dry during the procedure. In an alternative embodiment, it provides for such a dental device that also incorporates fiber optic technology to direct light into the working field, such light being used for enhanced visualization and for light-curing dental compounds.

BACKGROUND OF THE INVENTION

During the performance of various dental procedures, the dentist's continuous visualization of and access to all points within the patient's mouth is absolutely essential. A number of devices have long been used to retract the patient's lips and cheeks to provide such access. In the experience of this inventor, such devices have a tendency to be relatively complex in construction and in use. Similarly, suction tubes have long been used by practitioners to evacuate blood and saliva from the patient's mouth. Most frequently, the procedure being performed must be briefly interrupted to allow the dental assistant to insert the suction tube, evacuate the patient's mouth and then remove the tube, the dental assistant being in an almost continuous state of standby. What is needed is a device that combines the mouth retraction function as stated above with this suction capability.

In the experience of this inventor, such combined devices have also been attempted in the prior art. But again, such devices tend to lack simplicity in design, in manufacture and in functionality. For example, such attempts are disclosed in U.S. Pat. No. 4,019,255 issued to Cohen et al. and U.S. Pat. No. 5,037,298 issued to Hickham.

Accordingly, it is an object of the present invention to provide a new and useful dental device that combines mouth retraction capabilities with suction capabilities. It is another object to provide such a dental device that is simple in construction and easy to use. It is still another object to provide such a dental device that can be constructed to be disposable or nondisposable. It is yet another object to provide such a dental device that can be constructed to accommodate patient mouths of any size. It is still a further object to provide such a dental device that can incorporate fiber optic technology to provide a selective light source as such is desired or required by the particular procedure that is being performed.

SUMMARY OF THE INVENTION

The combined retractor and saliva ejector apparatus of the present invention has obtained these objects. It provides for a combined mouth retracting and saliva ejecting device having a forward suction portion, a right cheek retractor portion, a left cheek retractor portion, and a rearward suction portion. The device is functionally adapted and configured to be placed within the mouth of a dental patient. In the preferred embodiment, the device is constructed of a single piece of rigid, but resilient, tubular material, the material having an elastomeric memory. Although preferably cylindrical, it is to be understood that any tubular material, including a tubular material having an oblate or other cross section, could be used without deviating from the scope of this invention. The device can be constructed of material so as to be either disposable or nondisposable, the nondisposable version being capable of heat or chemical sterilization. The device can be made in almost any size to accommodate the wide variety of patients that it may be used with, including children. In an alternative embodiment, the device incorporates fiber optic technology whereby light transmissive fibers are imbedded into the device to allow for selective illumination within the patient's mouth as either a light source for light curable dental compounds or for enhanced visualization.

The foregoing and other features of the present invention will be apparent from the detailed description that follows.

BRIEF DESCRIPTION OF THE DRAWINGS

FIG. 1 is a front and slight bottom perspective view of a device constructed in accordance with the present invention and showing use of the device with a dental patient.

FIG. 2 is an enlarged front, top and right side perspective view of the device shown in FIG. 1.

FIG. 3 is a top plan view of the device shown in FIG. 2.

FIG. 4 is a rear elevational view of the device shown in FIG. 2.

FIG. 5 is a right side elevational view of the device shown in FIG. 2.

DETAILED DESCRIPTION

Referring now to the drawings in detail wherein like numbers represent like elements throughout, FIG. 1 illustrates a perspective view of one embodiment of the retractor and saliva ejector device, generally identified 10, constructed in accordance with the present invention. As shown, the device 10 includes several major portions. Specifically, the device 10 includes a forward suction portion 20, a right cheek retractor portion 40, a left cheek retractor portion 50, and a rearward suction portion 60. See FIG. 2. Referring again to FIG. 1, it will be seen that the device 10 is functionally adapted and configured to be placed within the mouth 90 of a dental patient. Details of this placement will be discussed later in this detailed description.

Referring now to FIG. 2, it will be seen that the device 10 is, in the preferred embodiment, constructed of a single piece of tubular material 12. Although preferably cylindrical, it is to be understood that any tubular material, including a tubular material having an oblate or other cross section, could be used without deviating from the scope of this invention. It is also preferable to use a plastic material that has sufficient resiliency to be bent slightly but provide adequate rigidity to allow the device to be used as a retractor within the patient's mouth 90. Thus, the material used should have elastomeric memory such that the device 10, even during use, is always attempting to return to its original formed shape and will, upon removal from the patient's mouth 90, return to that original shape. In the preferred embodiment, the device 10 is made of a single tubular piece of glycol modified polyethylene terephthalate (PETG). PETG is clear, tough and has good gas and moisture barrier properties. Some of this plastic is used in PETG soft drink bottles and other blow molded containers. In the preferred embodiment, the device 10 is disposable. It is to be understood, however, that the device 10 of the present invention could also be made of other materials having properties and characteristics similar to PETG, including a nondisposable material that can be sterilized by cold chemical sterilization or by heat sterilization techniques, without deviating from the scope of the invention.

It should also be apparent from the drawings that the device 10 is generally symmetrical along a central vertical plane. That is, the right and left portions of the device 10 are, in effect, mirror images of one another. See also FIGS. 3 and 4. Obviously, most patient mouths 90 are symmetrical. So too with a device that is placed within the mouth 90 for the purpose of balanced retraction. With respect to this detailed description, references made to right and left side of the device 10 will be from the orientation and perspective of the patient and his or her mouth 90, not from that of the observer.

Referring again to FIG. 2, it will be seen that the forward suction portion 20 of the device 10 includes a right side upright tubular first portion 22, an upwardly and outwardly extending second portion 24, a backward curved third portion 26 and an outward curved fourth portion 28. The right side components 22, 24, 26, 28 of the forward suction portion 20 form a flow continuum therethrough. Similarly, the forward suction portion 20 of the device 10 includes a left side upright tubular first portion 32, an upwardly and outwardly extending second portion 34, a backward curved third portion 36 and an outward curved fourth portion 38. The left side components 32, 34, 36, 38 of the forward suction portion 20 form a flow continuum therethrough. The right and left side upright first tubular portions 22, 32, respectively, terminate in a common air suction sleeve 14. The sleeve 14 is connected to an air suction source (not shown) of known technology.

Extending generally upwardly and outwardly from the left side and right side of the forward suction portion 20 is a right cheek retractor portion 40 and a left cheek retractor portion 50, respectively. The right cheek retractor portion 40 extends generally upwardly and outwardly from the outward curved fourth right side portion 28 of the forward suction portion 20. The right cheek retractor portion 40 includes an upwardly and inwardly curved first portion 42, an outwardly and more sharply curved second portion 44, a downwardly and inwardly curved third portion 46 and a backwardly extending and generally horizontal fourth portion 48. The right side components 42, 44, 46, 48 of the right cheek retractor portion 40 form a flow continuum therethrough. Similarly, the left cheek retractor portion 50 extends generally upwardly and outwardly from the outward curved fourth left side portion 38 of the forward suction portion 20. The left cheek retractor portion 50 includes an upwardly and inwardly curved first portion 52, an outwardly and more sharply curved second portion 54, a downwardly and inwardly curved third portion 56 and a backwardly extending and generally horizontal fourth portion 58. The left side components 52, 54, 56, 58 of the left cheek retractor portion 50 form a flow continuum therethrough as well. In the preferred embodiment, the flattened curve radius of the first cheek retractor portions 42, 52, and the flattened curve radius of the third cheek retractor portions 46, 56, are generally planar parallel, and the curve of the first and third cheek retractor portions 42, 52, 46, 56 need not be symmetrical. Those portions must be curvilinear so as to generally correspond to the contour of a patient's mouth 90. Upon insertion, the uppermost, or apex, portion 45, 55, of the right and left side cheek retractor portions 40, 50, respectively, will be closer in proximity to one another than are the lowermost and rearwardly extending fourth portions 48, 58 due to flexing that will occur within those portions of the device 10. The curve radius of the second portions 44, 54 of the right and left cheek retractor portions 40, 50, respectively, should be sufficient to accommodate a portion of the patient's lip therewithin. See FIG. 1. It is also to be understood that the various radii described herein are generally a function of overall size of the device 10 which is a function of the overall size of the patient's mouth 90. Accordingly, the device 10 of the present invention could be constructed in many different sizes so as to accommodate every patient size and age without deviating from the scope of the claims herein.

Extending generally rearwardly and outwardly from the fourth portion 48 of the right side cheek retractor portion 40 and rearwardly and outwardly from the fourth portion 58 of the left side cheek retractor portion 50 is a rearward suction portion 60. More specifically, the rearward suction portion 60 includes first right side portion 62 that extends generally rearwardly and outwardly from the fourth portion 48 of the right side cheek retractor portion 40. Curving inwardly from the first right side portion 62 is a second right side portion 64. A generally straight third right side 66 portion connects the second right side portion 64 to a forwardly and slightly downwardly curved fourth right side portion 68. Similarly, the rearward suction portion 60 includes first left side portion 72 that extends generally rearwardly and outwardly from the fourth portion 58 of the left side cheek retractor portion 50. Curving inwardly from the first left side portion 72 is a second left side portion 74. A generally straight third left side portion 76 connects the second left side portion 74 to a forwardly and slightly downwardly curved fourth left side portion 78. The fourth right and left side portions 68, 78, respectively, culminate in a curved fifth portion 82. The right side components 62, 64, 66, 68, the left side components 72, 74, 76, 78, and the fifth portion 82 of the rearward suction portion 60 form a flow continuum therethrough. The curved fifth portion 82 of the rearward suction portion 60 further includes a plurality of apertures 84 for suction of saliva and blood from the bottom of the patient's mouth therethrough. Although the apertures 84 are shown along the fifth portion 82 of the rearward suction portion 60, it is to be understood that the apertures 84 could be placed anywhere along the single piece 12 of tubular material to accomplish suction throughout the patient's mouth. Such aperture 84 placement is not a limitation of the present invention.

In application, and assuming that the patient has been properly sized for the device 10, the dental professional places the device 10 within the patient's mouth 90. This is accomplished by urging rearward suction portion 60 to the back of the mouth and by urging the right and left cheek retractor portions 40, 50, respectively, generally inwardly such that the gap created between the first and third right side portions 42, 46 and the gap created between the first and third left side portions 52, 56 capture a portion of the patient's upper lip to either side of the mouth 90. See FIG. 1. In this position, the forward suction portion 20 and the common air suction sleeve 14 simply rest on the patient's lower lip. The sleeve 14 is connected to an air suction source (not shown) of known technology. As the air suction source is actuated, saliva and blood are drawn into the plurality of apertures defined within the curved fifth portion 82 of the rearward suction portion 60 and through the flow continuum defined by the tube 12. This suction continues as long as the suction source remains actuated.

In an alternative embodiment, the tube 12 also includes one or more fiber optic cables (not shown) of known technology, the cables being imbedded just beneath the surface of outer periphery of the tube 12. The cables can be abraded at appropriate points along the tube 12 to disrupt the light continuum and provide illumination for the dental professional and for hardening light sensitive dental materials. A light source (also not shown) would be imbedded within the sleeve 14 and could be actuated as desired or required. For example, the dental professional, knowing which tooth he or she will be working on, abrades the correlating portion of the device 10. Following the placement of light sensitive dental material within the patient's mouth, the light source is actuated and light irradiates the material, thus allowing it to cure.

Based upon the foregoing, it will be seen that there has been provided a new and useful dental device that combines mouth retraction capabilities with suction capabilities; that is simple in construction and easy to use; that can be constructed to be disposable or nondisposable; that can be constructed to fit any size or age of patient; and that can incorporate fiber optic technology to provide a selective light source as such is desired or required by the particular procedure that is being performed.

The details of this invention having been described in accordance with the foregoing, I claim:

1. A retractor and saliva ejector apparatus that is insertable within the mouth of a dental patient which comprises a forward suction portion, a right cheek retractor portion, a left cheek retractor portion, and a rearward suction portion, wherein
   the forward suction portion is tubular and includes a right side upright first portion, a right side upwardly and outwardly extending second portion, a right side backward curved third portion and a right side outward curved fourth portion, all of which form a flow continuum therethrough, and
   the forward suction portion further includes a left side upright first portion, a left side upwardly and outwardly extending second portion, a left side backward curved third portion and a left side outward curved fourth portion, all of which form a flow a flow continuum therethrough,
   the right and left side upright first tubular portions terminating in a common air suction sleeve that is connectible to an air suction source.

2. The dental apparatus of claim 1 wherein
   the right cheek retractor portion and the left cheek retractor portion extend generally upwardly and outwardly from the left side and right side of the forward suction portion, respectively, and
   the right cheek retractor portion extends generally upwardly and outwardly from the outward curved fourth right side portion of the forward suction portion, the right cheek retractor portion including an upwardly and inwardly curved first portion, an outwardly and more sharply curved second portion, a downwardly and inwardly curved third portion and a backwardly extending and generally horizontal fourth portion, all of which form a flow continuum therethrough, and
   the left cheek retractor portion extends generally upwardly and outwardly from the outward curved fourth left side portion of the forward suction portion, the left cheek retractor portion including an upwardly and inwardly curved first portion, an outwardly and more sharply curved second portion, a downwardly and inwardly curved third portion and a backwardly extending and generally horizontal fourth portion, all of which form a flow continuum therethrough.

3. The dental apparatus of claim 2 wherein the first and third cheek retractor portions of the left cheek retractor portion have a curve radius, the first and third cheek retractor portions of the right cheek retractor portion have a like curve radius, and the curve radius of the first cheek retractor portions and the curve radius of the third cheek retractor portions are generally curvilinearly planar parallel, and the curve of the first and third cheek retractor portions are formed so as to generally correspond to the contour of the patient's mouth.

4. The dental apparatus of claim 3 wherein the curve radius of the second portions of the right and left cheek retractor portions, respectively, are configured to accommodate a portion of the patient's lip therewithin.

5. The dental apparatus of claim 4 wherein the size of the apparatus is a function of the overall size of the patient's mouth.

6. The dental apparatus of claim 3 wherein
   the rearward suction portion extends generally rearwardly and outwardly from the fourth portion of the right side cheek retractor portion and rearwardly and outwardly from the fourth portion of the left side cheek retractor portion, and
   the rearward suction portion includes a first right side portion that extends generally rearwardly and outwardly from the fourth portion of the right side cheek retractor portion, a second right side portion that curves inwardly from the first right side portion, a generally straight third right side portion, and a forwardly and slightly downwardly curved fourth right side portion,
   the rearward suction portion further includes a first left side portion that extends generally rearwardly and outwardly from the fourth portion of the left side cheek retractor portion, a second left side portion that curves inwardly from the first left side portion, a generally straight third left side portion, and a forwardly and slightly downwardly curved fourth left side portion, and
   the fourth right and left side portions culminating in a curved fifth portion, the right side components, the left side components, and the fifth portion of the rearward suction portion forming a flow continuum therethrough.

7. The dental apparatus of claim 6 wherein the curved fifth portion of the rearward suction portion includes a plurality of apertures for the suction of fluid therethrough.

8. The dental apparatus of claim 7 wherein a plurality of additional apertures are placed at various points along the apparatus for suction of fluid therethrough.

* * * * *